(12) United States Patent
Jung et al.

(10) Patent No.: US 10,758,248 B2
(45) Date of Patent: Sep. 1, 2020

(54) DIRECTION ADJUSTABLE SURGICAL TISSUE REMOVAL DEVICE

(71) Applicants: ENDOVISION CO., LTD., Daegu (KR); Min Ho Jung, Daegu (KR)

(72) Inventors: Min Ho Jung, Daegu (KR); Sang-Kyu Son, Busan (KR)

(73) Assignees: ENDOVISION CO., LTD., Daegu (KR); Min Ho Jung, Daegu (KR)

( * ) Notice: Subject to any disclaimer, the term of this patent is extended or adjusted under 35 U.S.C. 154(b) by 166 days.

(21) Appl. No.: 15/771,266

(22) PCT Filed: Apr. 16, 2018

(86) PCT No.: PCT/KR2018/004390
§ 371 (c)(1),
(2) Date: Apr. 27, 2018

(87) PCT Pub. No.: WO2019/098467
PCT Pub. Date: May 23, 2019

(65) Prior Publication Data
US 2019/0142437 A1 May 16, 2019

(51) Int. Cl.
*A61B 17/16* (2006.01)
*A61B 17/00* (2006.01)

(52) U.S. Cl.
CPC ...... *A61B 17/1604* (2013.01); *A61B 17/1608* (2013.01); *A61B 17/1631* (2013.01); *A61B 2017/0046* (2013.01); *A61B 2017/00477* (2013.01)

(58) Field of Classification Search
CPC ............ A61B 17/1604; A61B 17/1631; A61B 17/1608
See application file for complete search history.

(56) References Cited

U.S. PATENT DOCUMENTS

| | | | |
|---|---|---|---|
| 4,574,803 A * | 3/1986 | Storz | A61B 17/32001 606/171 |
| 4,777,948 A * | 10/1988 | Wright | A61B 17/1611 606/171 |
| 5,009,661 A * | 4/1991 | Michelson | A61B 17/1608 606/170 |

(Continued)

FOREIGN PATENT DOCUMENTS

KR  10-2015-0000455 A  1/2015

*Primary Examiner* — Andrew Yang
(74) *Attorney, Agent, or Firm* — Stein IP, LLC

(57) ABSTRACT

A direction adjustable surgical tissue removal device, including: an insert rod having a stopping step at a front end; a slider slidably coupled to the insert rod, moving forward and backward with respect to the stopping step, and having a punching portion forming a jaw in cooperation with the stopping step; a rotary shaft being a hollow member fixed behind the insert rod and rotated by a user; a pushing rod having a front end fixed to the slider sequentially through the rotary shaft and the insert rod and a rear end extending backward; a spring disposed between the rotary shaft and the rear end of the pushing rod and elastically supporting the pushing rod backward; and a handle accommodating a portion of the rotary shaft and moving the pushing rod forward such that the punching portion is pushed toward the stopping step.

10 Claims, 5 Drawing Sheets

(56) References Cited

U.S. PATENT DOCUMENTS

| | | | | |
|---|---|---|---|---|
| 5,273,519 A | * | 12/1993 | Koros | A61B 17/1611 606/170 |
| 5,484,441 A | * | 1/1996 | Koros | A61B 17/1611 606/79 |
| 5,879,365 A | * | 3/1999 | Whitfield | A61B 10/04 606/180 |
| 6,214,010 B1 | * | 4/2001 | Farley | A61B 17/1611 606/83 |
| 2004/0102783 A1 | * | 5/2004 | Sutterlin | A61B 17/1622 606/80 |
| 2004/0122433 A1 | * | 6/2004 | Loubens | A61B 17/1611 606/83 |
| 2008/0161809 A1 | | 7/2008 | Schmitz | 606/79 |

* cited by examiner ions. PCT/KR2018/004390, filed Apr. 16, 2018, which
DIRECTION ADJUSTABLE SURGICAL TISSUE REMOVAL DEVICE

CROSS-REFERENCE TO RELATED APPLICATIONS

This application is a national stage of International Application No. PCT/KR2018/004390, filed Apr. 16, 2018, which claims the benefit of priority to Korean Application No. 10-2017-0151636, filed Nov. 14, 2017, and Korean Application No. 10-2018-0011939, filed Jan. 31, 2018, in the Korean Intellectual Property Office, the disclosures of which are incorporated herein by reference.

BACKGROUND OF THE INVENTION

Field of the Invention

The present invention relates to a surgical tissue removal device and, more particularly, to a direction adjustable surgical tissue removal device that is simple to use and has high removal efficiency because the jaw for cutting off a tissue in a body can be freely turned even without changing the position of a handle.

Description of the Related Art

It is required to remove abnormal tissues or bones out of a body in many cases of various surgeries. For example, as for foraminal stenosis, the bone forming an intervertebral foramen grows and presses a nerve or a joint or a ligament hypertrophies in most cases, so the grown bone or hypertrophying tissues should be removed in a spinal surgery.

Other than a spinal surgery, it is required to remove abnormal tissues out of a body in many cases of laparoscopy. For example, when an abnormal tissue is found in a treatment process of inserting a trocar into the body of a patient and then inserting necessary surgical tools into the body through the trocar, an operator inserts a tool for removing a tissue through the trocar and removes the found tissue.

There are various surgical tissue removal devices, and as one of the devices, an "Articulating tissue cutting device (joint tissue cutting device)" has been disclosed in US2008/0161809. The cutting device is configured to widening an intervertebral foramen by cutting a hypertrophying tissue etc. in the intervertebral foramen with a blade at the free end after inserting the free end in the intervertebral foramen.

However, this device has a problem that the free end bends only in one direction with respect to the shaft. A handle, the shaft, and the free end are simply connected, so in order to bend the free end in the opposite direction, the user has to hold the handle in the opposite direction or has to twist the elbow and wrist about the shoulder in an inconvenient position. If an operator performs a surgery requiring precision in an inconvenient position, the surgical success rate is low and, in some cases, a fatal accident may occur.

DOCUMENTS OF RELATED ART

US Patent Application Publication No. US2008/0161809 (Articulating tissue cutting device)

Korean Patent Application Publication No. 10-2015-0000455 (Tissue removal device with adjustable delivery sleeve for neurosurgical and spinal surgery applications)

SUMMARY OF THE INVENTION

The present invention has been made in an effort to solve to problems and an object of the present invention is to provide a direction adjustable surgical tissue removal device that is convenient to use because a jaw that is inserted into a body can be freely turned even though a user holds a handle by hand.

A direction adjustable surgical tissue removal device according to an aspect of the present invention includes: an insert rod configured to be inserted toward a target point in a body in a surgery and having a stopping step at a front end; a slider slidably coupled to the insert rod, moving forward and backward with respect to the stopping step, and having a punching portion forming a jaw in cooperation with the stopping step; a rotary shaft being a hollow member fixed behind the insert rod and rotated by a user; a pushing rod having a front end fixed to the slider sequentially through the rotary shaft and the insert rod and a rear end extending backward; a spring disposed between the rotary shaft and the rear end of the pushing rod and elastically supporting the pushing rod backward; and a handle accommodating a portion of the rotary shaft such that the rotary shaft can be rotated therein and moving the pushing rod forward such that the punching portion is pushed toward the stopping step.

A hollow extension shaft having the same inner diameter as the rotary shaft may be further connected between the insert rod and the rotary shaft.

A tissue groove for temporarily keeping a tissue removed from a body may be formed on a side, which faces the punching portion, of the stopping step.

An included angle between a plane including the stopping step and a central axial line of the insert rod may be 100 to 130 degrees.

The rotary shaft may include: a shaft body having a constant diameter and extending in a longitudinal direction; a ring-shaped groove integrally formed at a rear end of the shaft body and having a diameter smaller than a diameter of the shaft body; and a locking ring disposed behind the ring-shaped groove and having holding grooves circumferentially arranged with regular angular intervals on an outer side thereof.

A pressing end to which a pressing force is applied from the handle may be formed at a rear end of the pushing rod.

The handle may include: a shaft support accommodating a portion of the rotary shaft and having a stopper, which stops rotation of the rotary shaft by being fitted in selected one of the holding grooves, on an inner side thereof; a fixed rod integrally formed with the shaft support and held by a user; a trigger linked to the fixed rod by a hinge pin and pulled to be turned by a user; and a road pusher disposed at an upper end of the trigger and pressing the pressing end when the trigger is pulled.

The holding grooves may be open toward the ring-shaped groove such that the holding grooves come out of the stopper and the ring-shaped groove is positioned to correspond to the stopper when the rotary shaft is pressed toward the shaft support.

A slit providing a path through which the stopper reaches the ring-shaped groove when the rotary shaft is inserted into the shaft support may be formed at the locking ring.

A moving indicator showing a position of the slit may be formed on an outer side of the rotary shaft, and a fixing indicator showing a position of the stopper may be formed on an outer side of the shaft support.

The direction adjustable surgical tissue removal device is convenient to use because the jaw that is inserted into a body can be freely turned even though a user holds a handle by hand.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, an embodiment of the present invention is described in detail with reference to accompanying drawings.

Figure 1:
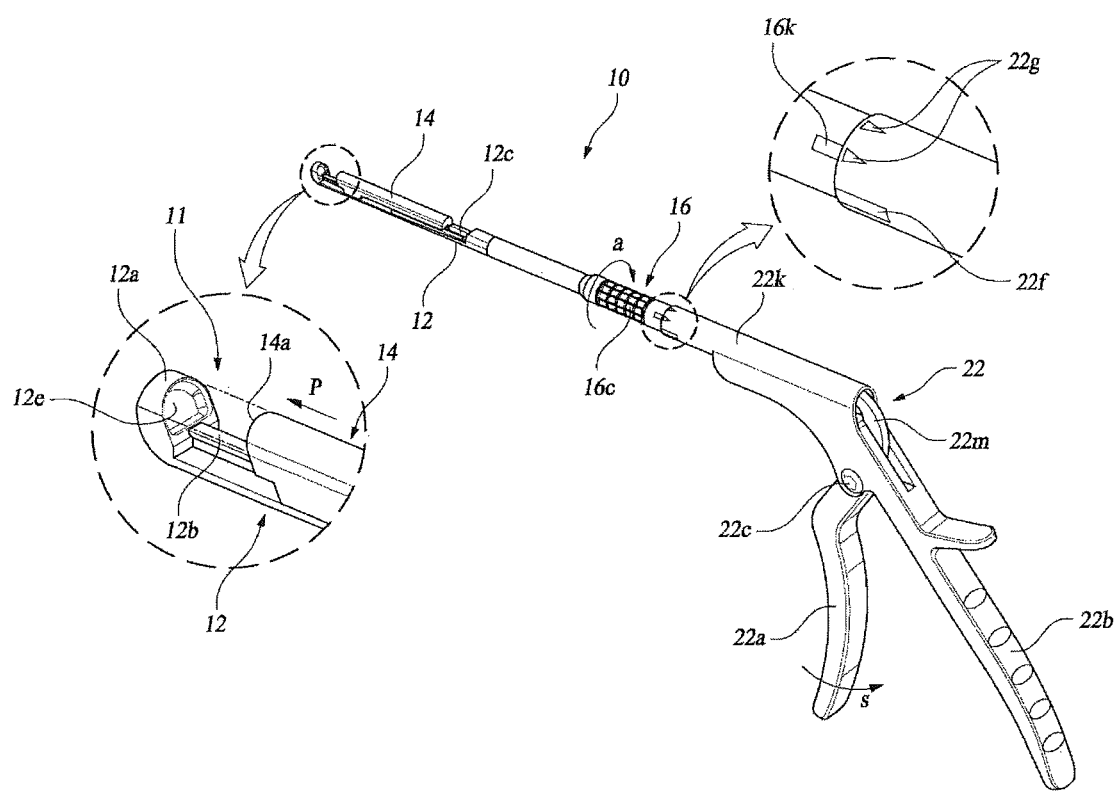
FIG. 1 is a perspective view showing the entire of a direction adjustable surgical tissue removal device according to an embodiment of the present invention.
Figure 2:
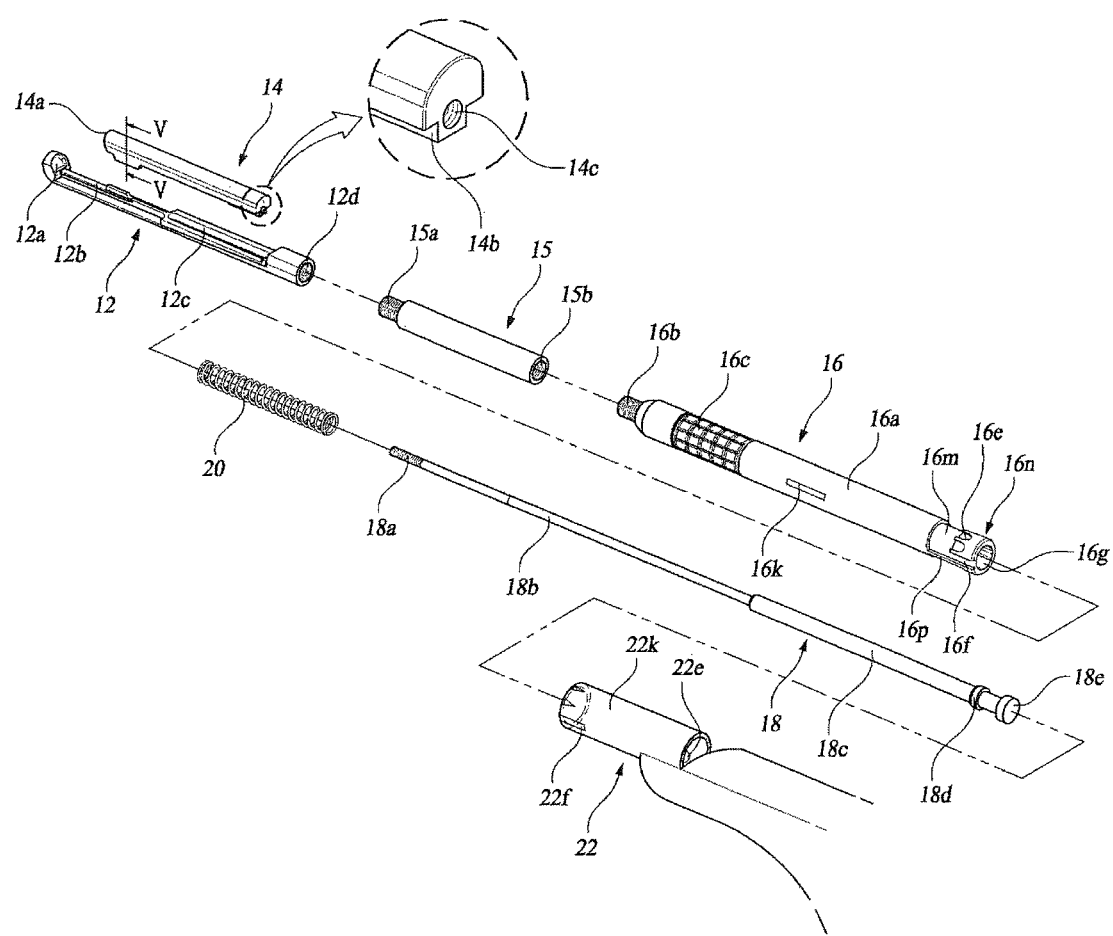
FIG. 2 is an exploded perspective view of the tissue removal device shown in FIG. 1.

FIG. 1 is a perspective view showing the entire of a direction adjustable surgical tissue removal device 10 according to an embodiment of the present invention and FIG. 2 is an exploded perspective view of the tissue removal device shown in FIG. 1.

A tissue stated herein means a part to be removed from a body, for example, a bone tissue including a cartilaginous tissue and an osseous tissue. However, tissues other than a bone tissue are included.

As shown in the figures, a tissue removal device 10 according to the embodiment includes an insert rod 12 that is inserted into a body in a surgery, a slider 14 that is coupled to the insert rod 12 to slide thereon, an extension shaft 15 that is coupled to the rear end of the insert rod 12, a rotary shaft 16 that is connected to the rear end of the extension shaft 15, a pushing rod 18 that is coupled to the slider 14 forward through the rotary shaft 16, a spring 20 that supports the pushing rod 18 backward, and a handle 22 that presses forward the pushing rod 18.

First, the insert rod 12 is a long straight member and has a stopping step 12a and a guide rail 12b. The stopping step 12a is formed at the front end of the insert rod 12 and constitutes a jaw 11 in cooperation with a punching portion 14a of the slider 14.

The jaw 11 is a part for picking an object to be removed out of a body. The insert rod 12 having this configuration is made of stainless steel and the front end is curved to be easily inserted into a body.

In particular, the jaw 11 can be rotated by rotating the rotary shaft 16 in the direction of an arrow 'a' or in the opposite direction. In particular, the jaw 11 is rotated with the handle 22 fixed. This is for removing difficulty where a user has to move the handle 22 such that the jaw 11 is aligned with a tissue to be removed.

Figure 6:
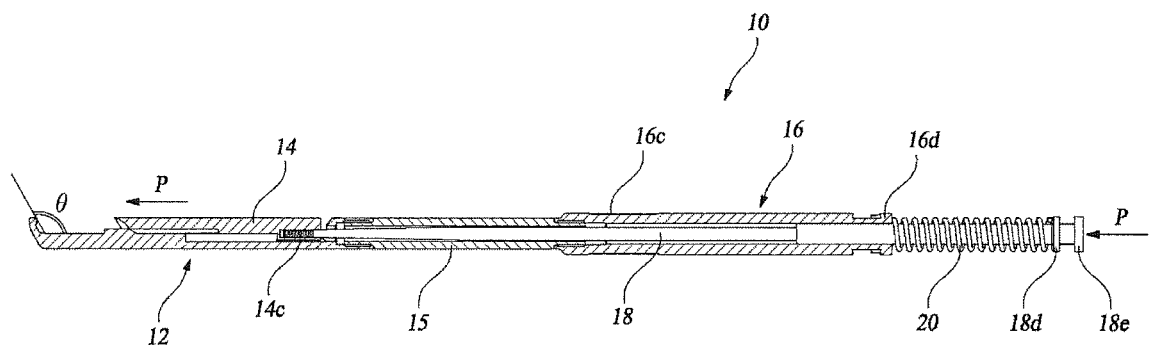
FIGS. 6 and 7 are cross-sectional views of the direction adjustable surgical tissue removal device shown in FIG. 1.

A tissue groove 12e is formed on the side, which faces the punching portion 14a, of the stopping step 12a. The tissue groove 12e is a space that temporarily keeps a removed tissue. The removed tissue put in the tissue groove 12e is taken out of a body while being covered with the punching portion 14a. In particular, as shown in FIG. 6, the included angle 9 between a virtual plane including the stopping step 12a and the central axial line of the insert rod is 100 to 130 degrees.

The guide rail 12b, which is a linear protrusion extending in the longitudinal direction of the insert rod 12, provides a path for straight reciprocation of the slider 14. The slider 14 moves forward and backward with respect to the stopping step 12a on the guide rail 12b.

A supporting groove 12c having a predetermined width and extending in the same direction is formed behind the guide rail 12b. The supporting groove 12c, which is a groove accommodating a sliding protrusion 14b formed on the bottom of the slider 14, also guides the slider 14 moving straight.

A female-threaded hole 12d is formed in the rear end of the insert rod 12. The female-threaded hole 12d is coupled to a male-threaded portion 15a of the extension shaft 15. Depending on cases, if the male-threaded portion 15a is not provided, the female-threaded hole 12d is coupled to a male-threaded portion 16b of the rotary shaft 16.

The slider 14 that is a part slidably coupled to the insert rod 12 has the punching portion 14a. The punching portion 14a corresponds to the stopping step 12a and pinches and fixes a tissue (hereafter, referred to a removal object) between the punching portion 14a and the stopping step 12a by pressing it to the stopping step 12a. The slider 14 may also be made of stainless steel.

Figure 5:
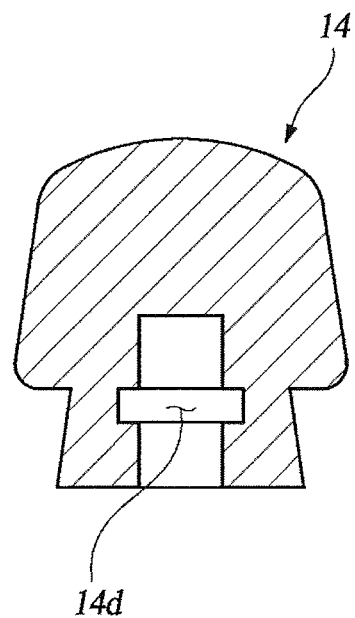
FIG. 5 is a cross-sectional view taken along line V-V of FIG. 2.

A rail groove 14d is formed on the bottom of the slider 14 in the shape shown in FIG. 5. The rail groove 14d accommodates the guide rail 12b, thereby slidably coupling the slider 14 to the rail groove 14d.

A rod hole 14c is formed in the rear end of the slider 14. The rod hole 14c is a female-threaded hole and is a part to which a slider coupling portion 18a of the pushing rod 18 is coupled.

The extension shaft 15 is a hollow pipe-shaped member having a constant diameter and has a male-threaded portion 15a and a female-threaded portion 15b at both ends, respectively. As described above, the male-threaded portion 15a is coupled to the female-threaded hole 12d of the insert rod 12. The female-threaded portion 15b is coupled to the male-threaded portion 16b of the rotary shaft 16. The extension shaft 15 is a part for increasing the entire length of the tissue removal device 10, but it may not be provided, if necessary. That is, the rotary shaft 16 may be directly coupled to the insert rod 12.

The rotary shaft 16 is a hollow member that is connected to the rear end of the extension shaft 15 behind the insert rod, when the extension shaft 15 is provided, and is also a member that is operated by a user. That is, a user can hold and rotate the rotary shaft 16 in the direction of the arrow 'a' or in the opposite direction by hand. To this end, a grip 16c that prevents slip is formed on the outer side of the rotary shaft 16. The reason of rotating the rotary shaft 16 is obviously for aligning the jaw 11 with a removal object.

The rotary shaft 16, which is a cylindrical member having the same diameter as the extension shaft 15, is composed of a shaft body 16a having the grip 16c, a ring-shaped groove 16m, and a locking ring 16n.

The shaft body 16a, which is a member coupled to the insert rod 12 through the male-threaded portion 16b, further has a moving indicator 16k on the outer side. The moving indicator 16k is a mark showing the position of a slit 16f to be described below to a user. The slit 16f is positioned on a line extending from the moving indicator 16k.

The slit 16f is a groove formed on the outer side of the locking ring 16n and is inserted in a shaft support 22k of the handle, so it is not visually shown and the moving indicator 16k is provided accordingly. As shown in FIG. 1, the moving indicator 16k is exposed from the front end of the shaft support 22k, so it can be visually shown.

The ring-shaped groove 16m has an outer diameter smaller than the outer diameter of the shaft body 16a. The ring-shaped groove 16m has a shape having a constant width and extending in the circumferential direction of the rotary shaft 16 and receives a stopper 22e when the rotary shaft 16b is rotated.

Though described below, the stopper 22d stops rotation of the rotary shaft 16 by being fitted in a selected holding groove 16e. Further, when the rotary shaft 16 is inserted into the shaft support 22k to be rotated, the stopper 22e is separated out of the holding groove 16e and positioned on the ring-shape groove 16m. When the stopper 22e is positioned on the ring-shaped groove 16m, the rotary shaft 16 can be freely rotated.

Figure 3:
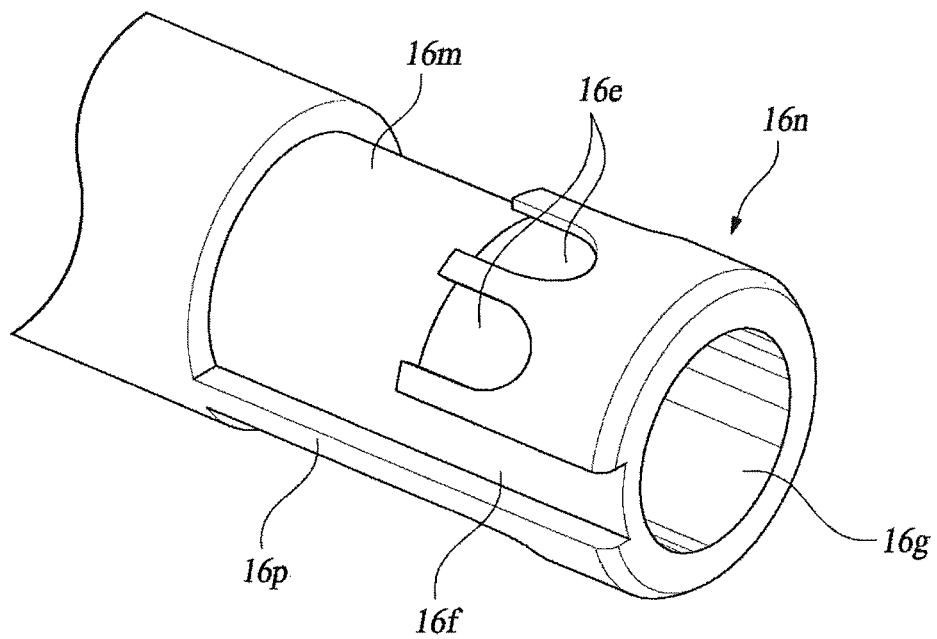
FIG. 3 is a view enlarging a locking ring shown in FIG. 2.
Figure 4:
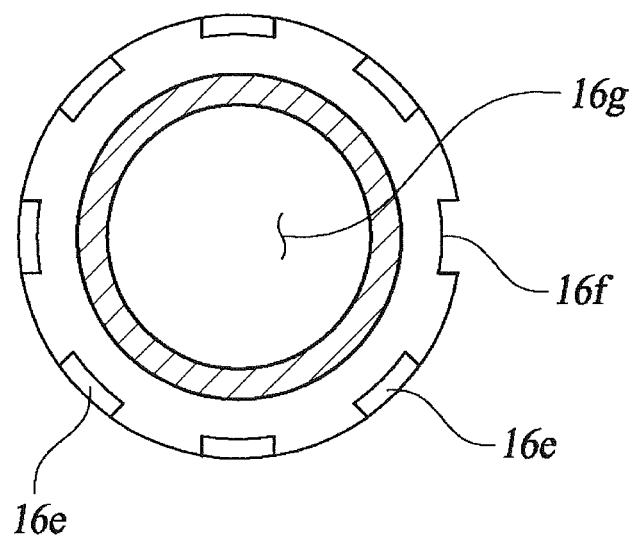
FIG. 4 is a view showing the locking ring at another angle.

The structure of the locking ring 16n is shown in more detail in FIGS. 3 and 4. FIG. 3 is a perspective view of the locking ring 16n. FIG. 4 is a view showing the locking ring 16n at another angle.

As shown in FIGS. 3 and 4, several holding grooves 16e, one slit 16f, and one anti-backward rotation step 19p is formed on the outer side of the locking ring 16n. The holding grooves 16e are arranged with regular angular intervals around the central axial line of a through-hole 16g and are open to the ring-shaped groove 16m.

The holding grooves 16e receive and lock the stopper 22 when the rotary shaft 16 is inserted in the handle 22. That is, the stopper 22e is fitted into one holding groove 16e selected from the holding grooves 16e. When the stopper 22e is fitted in any one of the holding grooves 16e, the rotary shaft 16 cannot be rotated and is prevented from separating from the shaft support 22k.

The slit 16f is a passage extending in the width direction of the locking ring 16n, that is, a direction perpendicular to the circumferential direction. The slit 16f functions as a passage through which the stopper 22e passes. For example, when the rotary shaft 16 that is not fixed is inserted into the shaft support 22k until the rear end of the locking ring 16n is locked to the rear end of the stopper 22e and then the rotary shaft 16 is further inserted with the slit 16f aligned the stopper 22e, the stopper 22e passes through the slit 16f. The stopper 22e that has completely passed through the slit 16f reaches the ring-shaped groove 16m, and in this state, when the rotary shaft 16 is rotated and released, the stopper 22e is pushed into a holding groove 16e by a spring 20. The anti-backward rotation step 16p prevents the rotary shaft 16 from being keeping rotated in one direction with the stopper 22e on the ring-shaped groove 22e.

Although the rotary shaft 16 is designed to be manually rotated in this embodiment, if necessary, the rotary shaft 16 may be configured to rotate with one click every time a trigger to be described below is pulled.

The way of separating the rotary shaft 16 from the shaft support 22k can also be changed. The rotary shaft 16 is separated with the slit 16f of the rotary shaft 16 aligned with the stopper 22e, but the device may be manufactured such that the rotary shaft 16 can be separated when it is pressed one more time with the slit 16f aligned with the stopper 22e.

The pushing rod 18 has an extension 18b longitudinally extending and having a slider coupling portion 18a, a spring fastening portion 18c extending from the extension 18b and fitted in the spring 20, and a spring supporting protrusion 18d and a pressing end 18e at the rear end portion of the spring fastening portion 18c.

The slider coupling portion 18a has a male thread on the outer side, so it is thread-fastened to the rod hole 14c. The slider 14 and the pushing rod 18 are moved together as a single unit. The spring fastening portion 18c, as shown in FIG. 6, is partially inserted in the rotary shaft 16 and supported by the inner side of the rotary shaft 16, so its straight motion is secured.

The spring supporting protrusion 18d supports a first end of the spring 20. Referring to FIG. 6, the first end of the spring 20 is supported by the spring supporting protrusion 18d and a second end is supported by the locking ring 16n. The spring 20 always elastically supports backward the pushing rod 18 and the slider 14 and is contracted by an external force applied in the direction of an arrow P.

The handle 22 is composed of the shaft support 22k, a fixed rod 22b, and a trigger 22a.

The shaft support 22k is a hollow tube-shaped part accommodating a portion of the rotary shaft 16. The rotary shaft 16 can be axially moved in the shaft support 22k. In particular, the stopper 22e is formed on the inner side of the shaft support 22k. The stopper 22e passes through the slit 16f of the rotary shaft 16 inserted in the shaft support 22k and is then fitted into a holding groove 16e across the ring-shaped groove 16m. For this loading process, a straight motion and a rotational motion of the rotary shaft and the action of the spring are needed, which was described above.

A fixing indicator 22f and sub-indicators 22g are disposed on the outer side at the front end of the shaft support 22k. The fixing indicator 22f is a mark showing the position of the stopper 22e. A virtual straight line including the fixing indicator 22f passes through the stopper 22e.

The sub-indicators 22g show the positions of the holding grooves 16e. For example, when the fixing indicator 22f and the moving indicator 16k are aligned, the holding grooves 16e are positioned at the positions indicated by the sub-indicators 22g. The sub-indicators 22g are helpful when the stopper 22e is inserted back into the holding grooves 16e after the rotary shaft 16 is rotated.

The fixed rod 22b, which integrally and diagonally extends from the shaft support 22k, is a part that comes in contact with a palm of a user. The design of the fixed rod 22b can be freely changed.

The trigger 22a, which is a part that a user pulls with fingers, is linked to the fixed rod 22b by a hinge pin 22c. In particular, a rod pusher 22m is integrally formed at the upper end of the trigger 22a. The rod pusher 22m is bent with a predetermined curvature and inserted forward from the rear of the shaft support 22k. When the trigger 22a is pulled and hinged in the direction of an arrow 's', the rod pusher 22m moves forward and pushes the pressing end 18e.

FIG. 5 is a cross-sectional view taken along line V-V of FIG. 2, which was described above.

Figure 7:
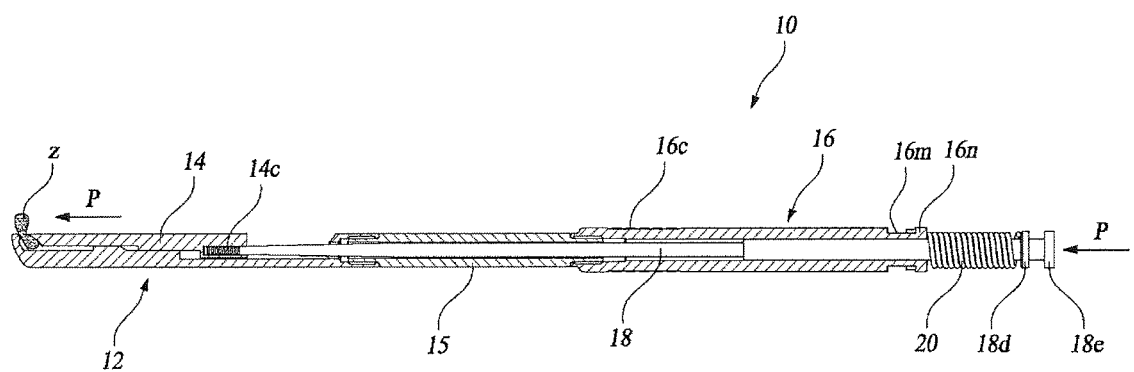

FIGS. 6 and 7 are cross-sectional views of the direction adjustable surgical tissue removal device 10 shown in FIG. 1.

As shown in FIG. 6, the pushing rod 18 has been maximally moved backward by the elasticity of the spring 20. Obviously, the punching portion 14a has also been positioned maximally away from the stopping step 12a.

In this state, a user inserts the tissue removal device 10 into a body and moves the jaw 11 close to a removal object. If necessary, the user rotates the rotary shaft 16 such that the removal object is positioned inside the jaw 11. Even though the rotary shaft 16 is rotated, the handle 22 is not rotated.

After the tissue removal device 10 is set through this process, the user moves the pushing rod 18 in the direction of the arrow P by pulling the trigger 22a of the handle 22. According to this process, the gap between the stopping step 12a and the punching portion 14a is decreased, and consequently, the removable removal object Z is pinched in the jaw 11. The user take off the removal object by moving the handle 22 and then takes out the tissue removal device 10 (with the trigger 22a pulled). The removal object Z is partially kept in the tissue groove 12e and cannot come out of the jaw 11.

When the user releases the trigger 22a after taking the tissue removal device 10 out of the body, the pushing rod 18 is moved backward by the spring and the removal object is separated from the jaw 11.

Although the present invention was described in detail through a detailed embodiment, the present invention is not limited thereto and may be modified in various ways by those skilled in the art without departing from the spirit of the present invention.

What is claimed is:

1. A direction adjustable surgical tissue removal device comprising:
   an insert rod configured to be inserted toward a target point in a body in a surgery and having a stopping step at a front end;
   a slider slidably coupled to the insert rod, moving forward and backward with respect to the stopping step, and having a punching portion forming a jaw in cooperation with the stopping step;
   a rotary shaft being a hollow member fixed behind the insert rod and configured to be rotatable manually;
   a pushing rod having a front end fixed to the slider sequentially through the rotary shaft and the insert rod and a rear end extending backward;
   a spring disposed between the rotary shaft and the rear end of the pushing rod and elastically supporting the pushing rod backward; and
   a handle accommodating a portion of the rotary shaft such that the rotary shaft can be rotated therein, and moving the pushing rod forward such that the punching portion is pushed toward the stopping step.

2. The device of claim 1, wherein a hollow extension shaft having the same inner diameter as the rotary shaft is further connected between the insert rod and the rotary shaft.

3. The device of claim 1, wherein a tissue groove for temporarily keeping a tissue removed from a body is formed on a side, which faces the punching portion, of the stopping step.

4. The device of claim 3, wherein an included angle between a plane including the stopping step and a central axial line of the insert rod is 100 to 130 degrees.

5. The device of claim 1, wherein the rotary shaft includes:
   a shaft body having a constant diameter and extending in a longitudinal direction;
   a ring-shaped groove integrally formed at a rear end of the shaft body and having a diameter smaller than a diameter of the shaft body; and
   a locking ring disposed behind the ring-shaped groove and having holding grooves circumferentially arranged with regular angular intervals on an outer side thereof.

6. The device of claim 5, wherein a pressing end to which a pressing force is applied from the handle is formed at a rear end of the pushing rod.

7. The device of claim 6, wherein the handle includes:
   a shaft support accommodating a portion of the rotary shaft and having a stopper, which stops rotation of the rotary shaft by being fitted in selected one of the holding grooves, on an inner side thereof;
   a fixed rod integrally formed with the shaft support and configured to be held manually;
   a trigger linked to the fixed rod by a hinge pin and configured to be pulled manually; and
   a road pusher disposed at an upper end of the trigger and pressing the pressing end when the trigger is pulled.

8. The device of claim 7, wherein the holding grooves are open toward the ring-shaped groove such that the holding grooves come out of the stopper and the ring-shaped groove is positioned to correspond to the stopper when the rotary shaft is pressed toward the shaft support.

9. The device of claim 8, wherein a slit providing a path through which the stopper reaches the ring-shaped groove when the rotary shaft is inserted into the shaft support is formed at the locking ring.

10. The device of claim 9, wherein a moving indicator showing a position of the slit is formed on an outer side of the rotary shaft, and
   a fixing indicator showing a position of the stopper is formed on an outer side of the shaft support.

* * * * *